(12) United States Patent
Schal et al.

(10) Patent No.: US 7,521,576 B2
(45) Date of Patent: Apr. 21, 2009

(54) PROCESS FOR THE DISTILLATION OF A MIXTURE OF ISOMERIC DIISOCYANATODIPHENYL-METHANES

(75) Inventors: Hans-Peter Schal, Dormagen (DE); Ulrich Wolf, Kerken (DE)

(73) Assignee: Bayer MaterialScience AG, Leverkusen (DE)

( * ) Notice: Subject to any disclaimer, the term of this patent is extended or adjusted under 35 U.S.C. 154(b) by 38 days.

(21) Appl. No.: 11/338,458

(22) Filed: Jan. 24, 2006

(65) Prior Publication Data

US 2006/0173206 A1 Aug. 3, 2006

(30) Foreign Application Priority Data

Jan. 29, 2005 (DE) .................. 10 2005 004 170

(51) Int. Cl.
*C07C 255/00* (2006.01)
(52) U.S. Cl. ...................................... 558/420
(58) Field of Classification Search ............... 558/420
See application file for complete search history.

(56) References Cited

U.S. PATENT DOCUMENTS

| 2,471,134 | A | 5/1949 | Wright | 196/100 |
| 4,189,354 | A | 2/1980 | Ellendt et al. | 203/81 |
| 2004/0171869 | A1 | 9/2004 | Reif et al | 560/347 |
| 2004/0236139 | A1 | 11/2004 | Schal et al. | 558/420 |

FOREIGN PATENT DOCUMENTS

DE 120 60 092 A1 7/2004

*Primary Examiner*—Jafar Parsa
(74) *Attorney, Agent, or Firm*—Lyndanne M. Whalen

(57) ABSTRACT

2,4'-MDI which contains very little 2,2'-MDI is prepared by distilling an isomeric starting mixture of diisocyanatodiphenylmethanes which includes 2,2'-diisocyanato-diphenylmethane, 2,4'-diisocyanatodiphenylmethane and 4,4'-diisocyanatodiphenyl-methane in at least one stage in a separating wall column. This distillation produces at least one mixture which contains 85 to 99 wt. % of 2,4'-diisocyanatodiphenylmethane, up to 15 wt. % of 4,4'-diisocyanatodiphenyl-methane and no more than 0.2 wt. % of 2,2'-diisocyanatodiphenylmethane.

4 Claims, 2 Drawing Sheets

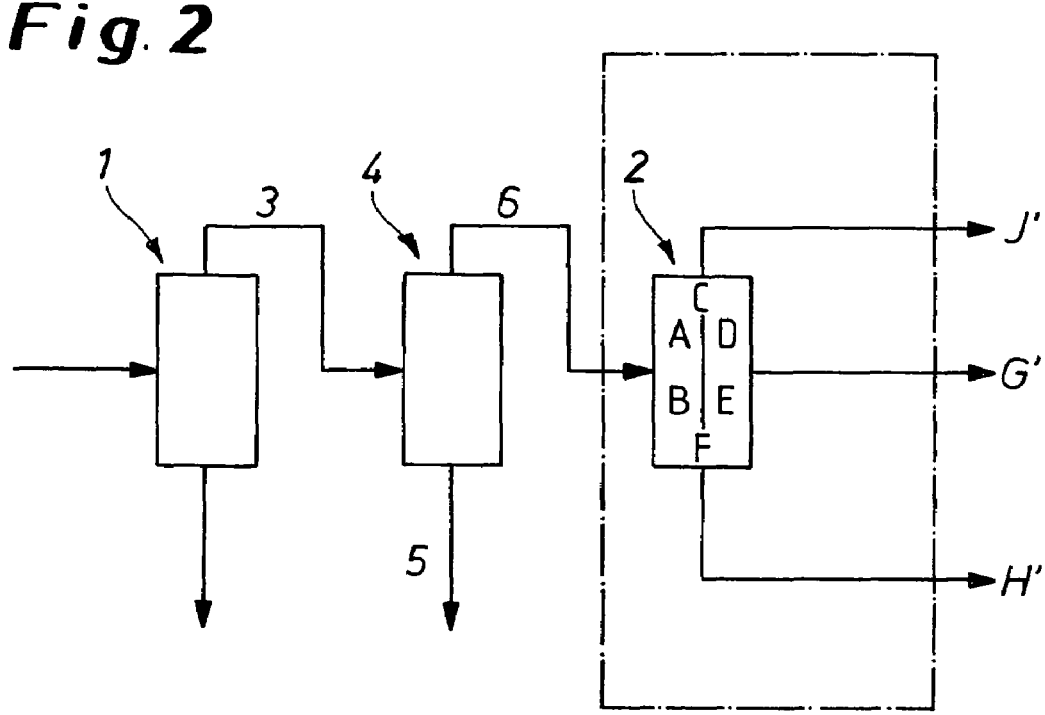
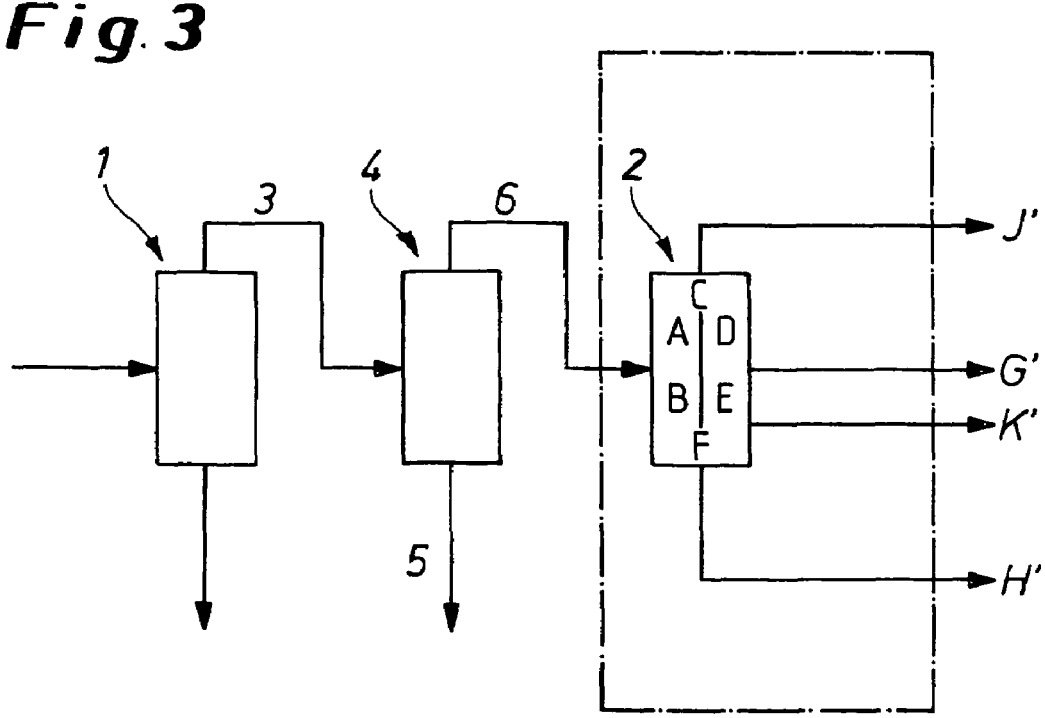

PROCESS FOR THE DISTILLATION OF A MIXTURE OF ISOMERIC DIISOCYANATODIPHENYL-METHANES

BACKGROUND OF THE INVENTION

The present invention relates to a process for the distillation of a mixture composed of at least 2,2'-diisocyanatodiphenylmethane (2,2'-MDI), 2,4'-diisocyanatodiphenyl-methane (2,4'-MDI) and 4,4'-diisocyanatodiphenylmethane (4,4'-MDI), in order to recover 2,4'-diisocyanatodiphenylmethane containing very little 2,2'-diisocyanato-diphenylmethane as well as mixtures of 4,4'- and 2,4'-diisocyanato-diphenylmethane containing very little 2,2'-diisocyanatodiphenylmethane.

Diisocyanatodiphenylmethane isomers are constituents of polyisocyanate mixtures of the diphenylmethane series which are produced during the phosgenation of aniline/formaldehyde condensates, also referred to herein as polyaminopolyphenyl-polymethanes.

The condensation of aniline and formaldehyde and the phosgenation of polyaminopolyphenylpolymethanes are sufficiently well disclosed in the prior art.

After the phosgenation of polyaminopolyphenylpolymethanes, phosgene is removed completely. Then the higher homologues of diisocyanatodiphenylmethane (also called polyisocyanatopolyphenylpolymethanes) are separated out. From the remaining mixture of isomeric diisocyanatodiphenylmethanes, mainly comprising 2,2'-diisocyanatodiphenylmethane, 2,4'-diisocyanatodiphenylmethane and 4,4'-diisocyanato-diphenylmethane (for simplification purposes also referred to herein as MDI-isomer mixtures or MDI crude mixtures), pure diisocyanatodiphenylmethane isomers or mixtures of two or three isomers can then be isolated, depending on the product specification required. A variety of isolation processes, based on a distillation or crystallization procedure or a combination of distillation and crystallization, are disclosed in the prior art.

For example, WO 02/070581 describes a process for preparing 2,4'-diisocyanato-diphenylmethane by isolation from a MDI crude mixture.

Furthermore, DE 2 631 168 A discloses a process for preparing diisocyanatodiphenyl-methane isomers, using a distillation process, by isolation from a polyisocyanate mixture obtained by the phosgenation of aniline/formaldehyde condensates. The useful materials 4,4'-diisocyanatodiphenylmethane and 2,4'-diisocyanatodiphenylmethane are obtained in this way. The isolation of 2,2'-diisocyanatodiphenylmethane is not described.

For many applications, the presence of 2,2'-diisocyanatodiphenylmethane in the useful materials or mixtures of useful materials is not desirable. However, during the simple distillation of crude diisocyanatodiphenylmethane mixtures, the isolation of 2,2'-MDI is impossible, or possible only in a technically difficult and economically costly manner.

SUMMARY OF THE INVENTION

The object of the present invention is to provide an economic and technically simple process for the distillation of a mixture of isomeric diisocyanatodiphenylmethanes which includes at least 2,2'-diisocyanatodiphenylmethane, 2,4'-diisocyanatodiphenylmethane and 4,4'-diisocyanatodiphenylmethane (hereinafter referred to as "the starting mixture") which enables the preparation of 2,4'-MDI which contains no 2,2'-MDI or at least has only a very small concentration of 2,2'-MDI of the order of magnitude of at most 0.2 wt. %.

This and other objects which will be apparent to those skilled in the art are accomplished by distilling the starting mixture in a separating wall column.

BRIEF DESCRIPTION OF THE DRAWINGS

FIG. 2 is a schematic diagram of a two stage distillation process within the scope of the present invention.

FIG. 3 is a schematic diagram of another two-stage distillation process within the scope of the present invention.

DETAILED DESCRIPTION OF THE INVENTION

Figure 1:
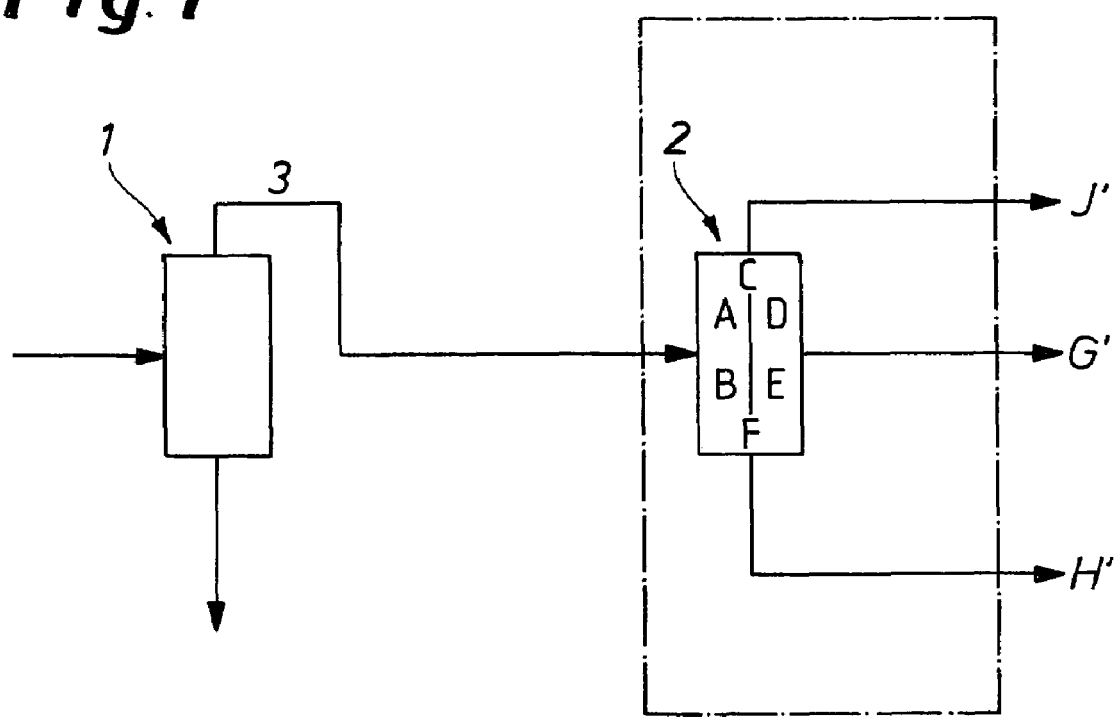
FIG. 1 is a schematic diagram of a one stage distillation process within the scope of the present invention.

The invention provides a process for preparing 2,4'-MDI which contains very little 2,2'-MDI by distilling a mixture of isomeric diisocyanatodiphenylmethanes which includes at least 2,2'-diisocyanatodiphenylmethane, 2,4'-diisocyanatodiphenylmethane and 4,4'-diisocyanatodiphenyhmethane in which the distillation is performed in at least one stage and a separating wall column is used in at least one distillation stage. This process produces at least one mixture which contains at most 0.2 wt. % 2,2'-diisocyanatodiphenylmethane, 85 to 99 wt. %, preferably 95 to 98 wt. %, most preferably 97.5 to 98 wt. % 2,4'-diisocyanatodiphenylmethane and at most 15 wt. % 4,4'-diisocyanatodiphenylmethane.

Unless stated otherwise, here and below any percentage data refer to percentages by weight, wherein the percentage data always relates to the composition of the isomers.

The mixture of isomeric diisocyanatodiphenylmethanes used as the starting mixture in the process according to the invention is produced during the phosgenation of polyaminopolyphenyl-polymethanes which are produced by the condensation of aniline and formaldehyde to give polyisocyanatopolyphenylpolymethanes. After phosgenation, which is preferably performed in monochlorobenzene (MCB) as solvent, the solvent and phosgene are first of all largely removed by distillation.

Then, using distillation in accordance with any of the known polymer separation procedures such as that disclosed in DE 2 631 168 A, a mixture of (1) polyisocyanato-polyphenylpolymethanes and diisocyanatodiphenylmethanes on the one hand and (2) the starting mixture of the three isomers 2,2'-diisocyanatodiphenylmethane, 2,4'-diisocyanatodiphenylmethane and 4,4'-diisocyanatodiphenylmethane on the other hand is obtained. Following this process step, the starting mixture may also contain: solvent, e.g. chlorobenzene, and other low-boiling compounds, e.g. phenyl isocyanate, with a proportion of less than 2 wt. %, at most 5 wt. % of polyisocyanatopolyphenylmethanes and also at most 5 wt. % of high molecular weight compounds which are produced as a result of thermal effects.

The process according to the invention is based on the separation by distillation of the MDI isomers from the starting mixture in a single-stage or multi-stage process using a separating wall column in at least one distillation stage. Using the process according to the invention, an MDI crude mixture can be separated into pure 2,4'-diisocyanato-diphenylmethane and a mixture of 2,4'-diisocyanatodiphenylmethane and 4,4'-diisocyanatodiphenylmethane. The separating wall column can be designed for different feed compositions and product specifications. On the other hand, for many application purposes, the concentration of 4,4'-MDI is of less importance, so the separation of 2,4'-MDI does not have to mean the complete separation of 4,4'-MDI. The advantage of the process according to the invention lies in the use of a separating wall column which is associated with lower production costs due to the lower engineering costs as compared with known distillation processes without separating wall columns.

The use of at least one separating wall column to obtain 2,4'-MDI from a mixture of isomeric diisocyanatodiphenylmethanes enables one or two distillation steps to be dispensed with, as compared with distillation processes according to the prior art. Thus, on the one hand the costs for equipment are considerably lower because, in addition to the distillation columns, additional heat-exchangers, piping, etc. can also be dispensed with, and on the other hand the energy costs are very greatly reduced because less heat has to be supplied. Furthermore, with a smaller number of distillation steps, the proportion of residues caused by reactions of the isocyanate groups is lower due to the lower heat input.

The distillation of a multicomponent mixture in a separating wall column is known, for example, from U.S. Pat. No. 2,471,134. In a separating wall column, the separating wall runs vertically up the middle section of the column. This means that the column is subdivided into four zones: a pre-fractionating zone and a main fractionating zone in the region of the separating wall as well as a bottom zone (stripping zone) and a rectifying zone (head zone). The multicomponent stream is fed to the prefractionating zone. In the following, the part of the prefractionating zone above the feed point is also called zone A and the part below the feed point is called zone B. The head product is withdrawn from the rectifying zone (zone C), the bottom product is withdrawn from the stripping zone (zone F). An intermediate product is withdrawn from the main fractionating zone, wherein the part of the main fractionating zone above the withdrawal point is also called zone D and the part below the withdrawal point is called zone E.

Normally, during a monomer/polymer separation, a 2-benzene-ring mixture is obtained which includes 0 to 5 wt. % of 2,2'-MDI, 5 to 15 wt. % of 2,4'-MDI and 80 to 95 wt. % of 4,4'-MDI. This type of mixture (also called the starting mixture) can be used in the distillation process of the present invention. In one embodiment of the process of the present invention, however, an additional distillation step is performed in which the MDI isomer mixture from monomer/polymer separation (the starting mixture) is fed to an isomer distillation stage (pre-separation by distillation). This additional distillation step, which is upstream of the distillation process carried out in the separating wall column, leads to a mixture which includes 0 to 15 wt. % of 2,2'-MDI, 12 to 60 wt. % of 2,4'-MDI and 25 to 88 wt. % of 4,4'-MDI. This can be used as a feed stream to the separating wall column. This mixture, which may serve as a feed stream to the separating wall column, preferably comprises at most 3% of 2,2'-MDI, 30 to 60 wt. % (e.g. 49.9%) of 2,4'-MDI and 40 to 70% (e.g. 46.9%) of 4,4'-MDI as well as traces of volatile compounds.

According to the process according to the invention, the starting material or the MDI isomer mixture is supplied to the separating wall column from the side in the region of the separating wall after preseparation by distillation. The separating wall is located in the middle region of the column and divides the cross-section of the column. The length of the separating wall depends on the process conditions and on the properties of the substance exchange elements used.

The number of separating stages required in the individual column sections depends on the process conditions, in particular on the composition of the feed stream and the products desired. Thus, for example, in the event of head and base specifications being designed for large-scale units, a substance exchange zone in the head part and the base part can be dispensed with and it can be minimized in the region of the separating wall.

In a particularly preferred embodiment, a separating wall length of about 6 to 8 m is produced when using a fabric packing with a specific surface area of, for example, 500 $m^2/m^3$. The substance exchange zones in the head and base of the column are each from 1.20 to 2.50 m, e.g. 1.80 m, long and each have from 6 to 12, e.g. 8 separating stages. The pre-fractionating zone has 10 to 14 separating stages above the feed point and 13 to 17 separating stages below the feed point. The main fractionating zone has 14 to 18 separating stages above the withdrawal point for the side stream and 12 to 16 separating stages below the withdrawal point.

All of the starting mixture or the MDI isomer mixture is supplied as a feed stream to the pre-fractionating zone of the separating wall column after pre-separation by distillation. The base stream from the separating wall column is supplied to an evaporator and partly evaporated. The vapor stream from the evaporator is recycled to the separating wall column and first of all flows through the packing in the base zone and is distributed to the pre-fractionating and main fractionating zones in accordance with the pressure conditions. The vapor streams from these zones are combined on leaving the separating wall zone and finally flow through the head zone. The vapors at the head of the separating wall column are condensed and 88 to 99.6%, preferably 98 to 99%, e.g. 98.5%, returns to the head zone. Below the head zone, 20 to 60%, preferably 30 to 50%, e.g. 40%, of the liquid running back passes into the pre-fractionating zone and 40 to 80%, preferably 50 to 70%, e.g. 60%, passes into the main fractionating zone. The side stream is initially fully withdrawn and then 60 to 97%, preferably 75 to 85%, e.g. 80%, is recycled to the main fractionating zone. The flow of vapor in the pre-fractionating zone and in the main fractionating zone is adjusted in accordance with the packing pressure losses. The overall pressure at the inlet and outlet regions of the separating wall is the same for both zones. If, for process engineering reasons, more vapor is intended to be admitted to one zone in the region of the separating wall, the cross-sections of the pre-fractionating zone and the main fractionating zone may also be chosen differently. The process can be optimized with regard to energy requirement by appropriate choice of the part cross-sections of the two zones.

Packings are especially suitable as substance exchange elements. However, other substance exchange elements which are well-known in distillation technology such as e.g. filler materials or plates, can also be used.

The separating wall column is operated under process conditions similar to those used in a column for a conventional distillation procedure, with regard to pressure and temperature. The absolute operating pressure for such a column is adjusted to 0.5 to 30 mbar, the head pressure being preferably 3 to 16 mbar. Depending on the composition of the mixture, the head temperature is 165 to 205° C. The pressure at the base is preferably 9 to 25 mbar with temperatures of 205 to 225° C.

During distillation of the mixture of isomeric diisocyanatodiphenylmethanes in the separating wall column, a stream which contains at least 80% of the 4,4'-diisocyanatodiphenylmethane introduced in the feed stream is discharged from the base. This base stream can be recycled to the separating wall column or to the polymer/monomer separation step. Depending on the feed stream, a mixture composed of 2,2'-diisocyanatodiphenylmethane (max. 80 wt. %), 2,4'-diisocyanato-diphenyl-methane (18 to 80 wt. %) and 4,4'-diisocyanatodiphenylmethane (max. 2 wt. %) is obtained as the head product and a mixture composed of 2,4'-diisocyanatodiphenyl-methane and 4,4'-diisocyanatodiphenylmethane in the ratio by weight of 99:1 to 85:15 is obtained as the side stream. According to the invention, it is important that the concentration of 2,2'-MDI in the side stream is very small, i.e. at most 0.2 wt. %, preferably at most 0.1 wt. %.

In a particularly preferred embodiment of the process of the present invention, a mixture of 95 to 98 wt. % of 2,4'-MDI and at most 15 wt. % of 4,4'-MDI, in particular 1 to 5 wt. % of 4,4'-MDI is withdrawn in the side stream. The concentration of 2,4'-MDI in the side steam can be varied between the limits of 95 to 99 wt. % by suitable distribution of liquid between the pre-fractionating zone and the main fractionating zone. The reflux ratio in the head is adjusted in particular to be within the range of from 7.5 to 250, but is more preferably in the range of from 30 to 90, with the head stream amounting to from 2 to 12 wt. %, with respect to the feed stream. The base stream amounts to 20 to 85 wt. %, preferably 40 to 60 wt. %, of the feed stream.

Alternatively, the process of the present invention can also be performed with a further side stream withdrawal point below the first side stream withdrawal point.

The second side stream withdrawal point is then also in the main fractionating zone. A mixture of 4,4'-MDI and 2,4'-MDI containing 18 to 82 wt. % of 2,4'-MDI can be withdrawn here. Most preferably, a commercially useful mixture of 50 to 60 wt. % of 2,4'-MDI with at most 0.2 wt. % of 2,2'-diisocyanatodiphenylmethane is withdrawn.

In the process of the present invention, the main product, that is largely pure 2,4'-MDI, is withdrawn from the separating wall column in the main fractionating zone, as the side stream. The amount of side stream is preferably at least 3 wt. % of the feed stream. More preferably, the proportion of the side stream is from 38 to 50 wt. %, e.g. 44 wt. %, of the feed stream. The main product is preferably composed of from 85 to 99 wt. % of 2,4'-MDI and at most 15 wt. %, preferably, 1 to 15 wt. %, of 4,4'-MDI, wherein the proportion of 2,2'-MDI is at most 0.2 wt. %. Most preferably, the product in the side stream is a mixture of 95 to 98 wt. % of 2,4'-MDI and 2.5 to 5 wt. % of 4,4'-MDI, wherein the proportion of 2,2'-MDI is at most 0.2 wt. %. The base product is preferably composed of from 2 to 35 wt. % of 2,4'-MDI and 65 to 98 wt. % of 4,4'-MDI, more preferably, from 8 to 12 wt. % of 2,4'-MDI and 88 to 92 wt. % of 4,4'-MDI. In this case, the base product can be recycled to the upstream distillation step (pre-separation by distillation). The head product is preferably composed of from 20 to 67 wt. % of 2,2'-MDI and 33 to 80 wt. % of 2,4'-MDI, wherein the proportion of 4,4'-MDI is at most 2 wt. %.

In a first embodiment of the present invention which is illustrated in FIG. 1, distillation of the MDI isomer mixture is performed in one stage using a separating wall column. Here, a MDI crude mixture from the polymer/monomer separation procedure (starting mixture) is supplied to the separating wall column in the mid-region of the separating wall. In particular, chlorine-containing volatile components, solvent and the greatest part of the 2,2'-MDI are transferred to zone C via zone A. Furthermore, a proportion of the 2,4'-isomer is transported into this zone and, depending on the reflux ratio being set, is either withdrawn via the head or is pushed into zone D. In zone D, this fraction meets a stream which passes the separating wall at the lower end and experiences pre-separation into 2,4'-MDI and 4,4'-MDI via zones B and E.

Depending on the withdrawal point in the main fractionating zone, i.e. in the regions D, E, either different isomer mixtures, composed of 2,2'-, 2,4'- and 4,4'-MDI, or else pure isomers, are withdrawn. In this case, pure isomers are understood to be isomers which are commercially useful and require no further separation.

In a second embodiment of the present invention which is illustrated in FIG. 2, the crude distillation stream from the polymer/monomer separation procedure (starting mixture) is first separated on a first column into a head stream, composed of volatile components, 2,2'-MDI, 2,4'-MDI and 4,4'-MDI and a base stream composed of residues of 2,4'-MDI and the major proportion of 4,4'-MDI.

The base stream from this first distillation stage without a separating wall column can be separated on a downstream column, in any known manner, into a head stream composed of pure 4,4'-MDI and a base stream, wherein the latter can be recycled, e.g. to the polymer/monomer separation procedure.

The head stream from the first distillation stage is used to recover 2,4'-MDI containing very little 2,2'-MDI and a 2,4'-/4,4'-MDI mixture containing very little 2,2'-MDI, using a separating wall column. For this purpose, this head stream is fed to the pre-fractionating zones A, B of a separating wall column. A stream of low-boiling components containing the greater part of the 2,2'-MDI introduced with the feed stream is withdrawn at the head of the separating wall column, whereas 2,4'-MDI containing very little 2,2'-MDI (max. 0.2% 2,2'-MDI) with a low concentration of 4,4'-MDI (max. 5%) can be withdrawn from the main fractionating zones D, E. A stream which contains about 90% 4,4'-MDI and about 10% 2,4'-MDI is produced at the base of the separating wall column and this can be taken to a crystallization procedure or to another separation by distillation procedure for purification and recovery of 4,4'-MDI.

In a third embodiment of the present invention which is illustrated in FIG. 3, the MDI isomer mixture is also distilled in two stages with a separating wall column in the second stage. In a manner similar to that described for the two-stage process illustrated in FIG. 2, the crude distillation stream from the polymer/monomer procedure (starting mixture) is first separated into a head stream composed of volatile components, 2,2'-MDI, 2,4'-MDI and 4,4'-MDI and a base stream composed of residues of 2,4'-MDI and the major proportion of 4,4'-MDI.

The base stream from the first distillation stage can again be separated, in a downstream column in any known manner, into a head stream composed of pure 4,4'-MDI and a base stream, wherein the latter can be recycled, for example, to the polymer/monomer distillation procedure.

The head stream from the first distillation stage is used in the same way as in the two-stage distillation in accordance with FIG. 2 described previously for the recovery of 2,4'-MDI containing very little 2,2'-MDI and a 2,4'-/4,4'-MDI mixture containing very little 2,2'-MDI in a separating wall column. For this purpose, the head stream from the first distillation stage is fed to the pre-fractionating zone A, B in a separating wall column. A stream of low-boiling components which contains the greatest part of the 2,2'-MDI fed with the feed stream is withdrawn at the head of the separating wall column, while a first side stream composed of 2,4'-MDI containing very little 2,2'-MDI (max. 0.2% 2,2'-MDI) with a low concentration of 4,4'-MDI (max. 15%) is withdrawn from the main fractionating zone D, E. Unlike the two-stage distillation illustrated in FIG. 2, in the third embodiment of the invention (FIG. 3), an additional 2,2'-MDI-deficient side stream, more preferably composed of from 50 to 60% of 2,4'-MDI is also withdrawn in the main fractionating zone D, E, below the withdrawal point for 2,4'-MDI containing very little 2,2'-MDI.

A stream which contains about 90% 4,4'-MDI and about 10% 2,4'-MDI is produced at the base of the column and can be taken, for example, to a crystallization procedure or to another separation by distillation procedure for purification and recovery of 4,4'-MDI.

EXAMPLES

Example 1

A one-stage distillation using a separating wall column was performed in accordance with the embodiment of the invention illustrated in FIG. 1. Fabric packings with 500 $m^2/m^3$ specific surface area were used as substance exchange elements in the separating wall column. 40 wt. % of the liquid was introduced to the pre-fractionating zone and 60 wt. % to the main fractionating zone. The rectifying zone and the stripping zone each had 8 separation steps, the pre-fractionating zone had 12 separation steps at the top and 14 separation steps at the bottom, the main fractionating zone had 16 separation steps at the top and 14 separation steps at the bottom, wherein the separation steps at the top and at the bottom, here and in the following, mean the separating steps above and below the supply point for the feed stream in the pre-fractionating zone or above and below the side stream withdrawal point in the main fractionating zone. The head pressure was 6 mbar. The reflux ratio at the distillate withdrawal point was 56:1, the reflux ratio at the side stream withdrawal point was 3.7:1.

12.5 kg/h of an isomer mixture composed of 3.0 wt. % 2,2'-MDI, 50.0 wt. % 2,4'-MDI and 47.0 wt. % 4,4'-MDI were fed to the separating wall column within the pre-fractionating zone, at the 13th step from the top. Three product streams were withdrawn from the separating wall column: 0.6 kg/h of a head stream composed of 56.4 wt. % 2,2'-MDI, 43.5 wt. % 2,4'-MDI and 0.1 wt. % 4,4'-MDI; 5.5 kg/h of a side stream composed of 0.1 wt. % 2,2'-MDI, 97.5 wt. % 2,4'-MDI and 2.4 wt. % 4,4'-MDI; and 6.4 kg/h of a base stream with an isomer purity of 90 wt. % of 4,4'-MDI and 10 wt. % 2,4'-MDI. The side stream was withdrawn after the 16th separation step in the main fractionating zone.

Example 2

A one-stage distillation using a separating wall column was performed in a manner analogous to that of the embodiment of the invention illustrated in FIG. 1. Fabric packings with a specific surface area of 500 $m^2/m^3$ were used as substance exchange elements in the separating wall column. 50 wt. % of the liquid was introduced to the pre-fractionating zone and 50 wt. % to the main fractionating zone. The rectifying zone and the stripping zone each had 8 separation steps, the pre-fractionating zone had 12 separation steps at the top and 14 separation steps at the bottom, the main fractionating zone had 16 separation steps at the top, 12 separation steps in the middle and 2 separation steps at the bottom. The head pressure was 6 mbar. The reflux ratio at the distillate withdrawal point was 72:1, the reflux ratio at the upper side stream withdrawal point was 8.2:1, the reflux ratio at the lower side stream withdrawal point was 3.9:1. The upper side stream was withdrawn after the 16th separating step in the main fractionating zone. The lower side stream was withdrawn after the 28th separating step in the main fractionating zone. The head pressure was 6 mbar. The reflux ratio at the distillate withdrawal point was 75:1, the reflux ratio at the upper side stream withdrawal point was 9.3:1, the reflux ratio at the lower side stream withdrawal point was 4.0:1.

11 kg/h of an isomer mixture composed of 3.0 wt. % 2,2'-MDI, 50.0 wt. % 2,4'-MDI and 47.0 wt. % 4,4'-MDI were fed to the separating wall column within the prefractionating zone, at the 13th step from the top, in the region of the separating wall. Four product streams were withdrawn from the separating wall column: 0.6 kg/h of a head stream composed of 53.3 wt. % 2,2'-MDI, 46.6 wt. % 2,4'-MDI and at most 0.1 wt. % 4,4'-MDI; 2.6 kg/h of an upper side stream composed of 0.1 wt. % 2,2'-MDI, 97.5 wt. % 2,4'-MDI and 2.4 wt. % 4,4'-MDI; 4.5 kg/h of a lower side stream composed of 0.07 wt. % 2,2'-MDI, 55 wt. % 2,4'-MDI and 44.93 wt. % 4,4'-MDI; and, 3.3 kg/h of a base stream with an isomer purity of 92.8 wt. % of 4,4'-MDI of and 7.2 wt. % 2,4'-MDI.

Although the invention has been described in detail in the foregoing for the purpose of illustration, it is to be understood that such detail is solely for that purpose and that variations can be made therein by those skilled in the art without departing from the spirit and scope of the invention, except as it may be limited by the claims.

What is claimed is:

1. A process for preparing 2,4'-MDI which contains very little 2,2'-MDI comprising distilling an isomeric starting mixture of diisocyanatodiphenylmethanes comprising 2,2'-diisocyanatodiphenylmethane, 2,4'-diisocyanatodiphenylmethane and 4,4'-diisocyanatodiphenylmethane in a separating wall column to obtain at least one product mixture comprising 85 to 99 wt. % of 2,4'-diisocyanatodiphenylmethane, up to 15 wt. % of 4,4'-diisocyanatodiphenylmethane and up to 0.2 wt. % of 2,2'-diisocyanatodiphenylmethane.

2. The process of claim 1 in which a second product mixture comprising 4,4'-MDI and from 18 to 82 wt. % of 2,4'-MDI is obtained.

3. The process of claim 1 in which a second product mixture comprising 4,4'-MDI, from 50 to 60 wt. % of 2,4'-MDI and up to 0.2 wt. % of 2,2'-MDI is obtained.

4. The process of claim 1 in which the distillation is performed in two stages, the separating wall column is used in the second stage, and the starting mixture distilled in the separating wall column is a distillate from the first stage.

* * * * *